United States Patent [19]
Johansson

[11] 4,426,358
[45] Jan. 17, 1984

[54] FAIL-SAFE DEVICE FOR A LID OF A PRESSURE VESSEL

[76] Inventor: Arne I. Johansson, Fågelvägen 5, 840 70 Hammarstrand, Sweden

[21] Appl. No.: 372,773

[22] Filed: Apr. 28, 1982

[51] Int. Cl.³ .............................. A61L 2/06; G05B 9/00; G05D 16/00
[52] U.S. Cl. ..................... 422/112; 49/394; 49/449; 422/114; 422/116; 422/117; 422/118; 422/296
[58] Field of Search ............... 422/117, 118, 112, 116, 422/26, 113, 114, 296; 49/394, 449

[56] References Cited

U.S. PATENT DOCUMENTS

| 2,112,639 | 3/1930 | Underwood | 422/116 |
|---|---|---|---|
| 3,454,352 | 7/1969 | Lamboy et al. | 422/26 X |
| 3,574,529 | 4/1971 | Larro | 422/116 X |
| 3,876,385 | 4/1975 | Markus et al. | 422/118 |
| 3,944,387 | 3/1976 | Schreckendgust | 422/114 X |
| 4,256,701 | 3/1981 | Johansson | 422/242 |
| 4,309,381 | 1/1982 | Chamberlain et al. | 422/116 X |

FOREIGN PATENT DOCUMENTS

| 77789 | 7/1954 | Denmark | 422/118 |
|---|---|---|---|
| 2741644 | 3/1979 | Fed. Rep. of Germany | 422/118 |
| 2743237 | 4/1979 | Fed. Rep. of Germany | 422/118 |
| 2044307 | 10/1980 | United Kingdom | 422/118 |
| 2074872 | 11/1981 | United Kingdom | 422/118 |
| 613801 | 7/1978 | U.S.S.R. | 422/118 |

Primary Examiner—Barry S. Richman
Attorney, Agent, or Firm—Pollock, Vande Sande & Priddy

[57] ABSTRACT

A fail-safe device for a pressure vessel includes a blocking device for a lid thereof, which blocking device is locked by means of a first locking device sensing the internal pressure in the vessel. This device in its turn is provided with a second locking device which works independently by sensing pressure or temperature inside the vessel and locks the first locking device in its locked position whenever pressure or temperature is dangerously high inside the vessel. The object is to assure a safe closing of the lid which is both foolproof and fail-safe.

5 Claims, 3 Drawing Figures

FAIL-SAFE DEVICE FOR A LID OF A PRESSURE VESSEL

BACKGROUND OF THE INVENTION

The present invention is applicable to a pressure vessel and to problems of personnel security regarding pressure vessels. The invention is particularly suitable for autoclaves used for sterilizing purposes, where a lid must be opened and closed at short intervals for loading and emptying of various goods and instruments. However, the invention is useful in all kinds of pressurized vessels where a lid has to be opened and closed with some frequency.

Maneuvering pressure vessel lids is potentially dangerous, as there may be a residual pressure of some magnitude, in which case the lid should not be liberated for personnel security reasons. This is particularly so for pressurized vessels containing hot steam, which can cause substantial harm if the lid is opened rashly.

OBJECTS OF THE INVENTION

An object of the present invention is a so-called fail-safe device for the lid of a pressure vessel. By "fail-safe" is intended the feature of double safety, such that two or more independent safety measures are introduced, so that, if one of them fails, there will be another safety function. Even if each of the safety measures is reasonably sure to work, this is not sufficient as pressure vessels must be considered as potentially dangerous. If there are two safety devices, each of them reasonably sure to function at all times, the probability that both of them will malfunction simultaneously is really insignificant, and the safety factor of the system increases substantially. If two independent safety devices are each considered to malfunction only once in 10,000 cases, the two of them in combination will malfunction only once in a hundred million cases.

It is a particular object of the invention to provide a fail-safe device for the lid of a steam-pressurized vessel, in particular such a vessel of the kind used for sterilization purposes, e.g., in hospitals.

One such construction of an autoclave with a lid or hatch, for which the present invention is valuable, is disclosed in U.S. Pat. No. 4,256,701, which disclosure is hereby included by reference.

SUMMARY OF THE INVENTION

The invention relates to a fail-safe device for a lid of a pressure vessel, the lid having a blocking mechanism for blocking the lid against opening from internal pressure in the vessel, which blocking mechanism is switchable from a blocking state to an unblocking state for enabling the lid to be opened, said fail-safe device comprising a first locking device switchable between a locking position for locking the blocking mechanism in said blocking state and an unlocking position where said blocking mechanism is unlocked, a displacement device communicating with the inside of the vessel and coupled to displace said first locking device against resilient means into said locking position when a predetermined pressure prevails inside the vessel, a sensor for sensing a predetermined condition inside the vessel and for emitting an electrical signal when said condition arises, an electromechanical transducer coupled to receive said electrical signal for generating a force, and a second locking device coupled to said electromechanical transducer for moving into a locking position for locking said first locking device in its said locking position when receiving said force.

According to a preferred embodiment, the pressure vessel is provided with venting means including an electromechanical valve which opens when there is a mains failure.

DESCRIPTION OF A PREFERRED EMBODIMENT

An embodiment of the invention will now be described, corresponding to the best mode known. Although in practice and in the embodiment used it cooperates with an autoclave as described in U.S. Pat. No. 4,256,701, schematic FIG. 1 is used to explain the invention.

Figure 1:
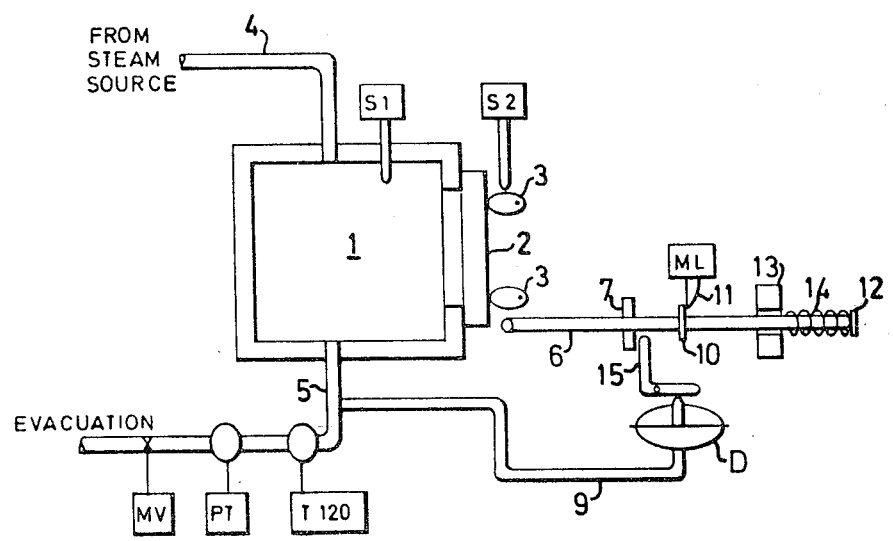
FIG. 1 shows a schematic drawing of an autoclave having a lid which is protected according to the invention.

In FIG. 1 is shown schematically a pressure vessel 1 having a removable lid 2 with a sealing O-ring (not shown) and a device for tightening and blocking the lid in place. This blocking mechanism is shown as two rotatable excenters 3, which may be mechanically coupled to a handle for tightening. In a preferred embodiment it is preferred to block by turning the excenters over their "dead points", so that opening can only be made by first pressing in the lid slightly, whereby a pressure inside will create a noticeable counterforce and make unblocking at least difficult when vessel 1 is pressurized.

There is an entry pipe 4 for introducing steam from a boiler (not shown) and an evacuation pipe 5 for emptying air and condensed water. This evacuation pipe has an electromagnetic valve mv, a pressure sensor PT and a thermostat switch T120.

In FIG. 1 there is also shown a sensor S1 for sensing a predetermined condition inside the vessel. Generally speaking, this sensor S1 may be a pressure sensor, but when working with a steam-sterilizing autoclave it is preferred to use a temperature sensor which signals that hot steam is present by closing a switch. This sensor S1 may preferentially be mounted near the entry of pipe 4 or even connected to pipe 4.

Cooperating with the blocking mechanism 3 there is a sensor S2, which may be a microswitch, for sensing that the blocking mechanism is in its blocking state and thus that the autoclave is closed.

There is also a first locking device 6 which, when locked, locks the blocking mechanism in its blocking state. Although only schematically indicated, locking device 6 is a bar which in its position indicated in FIG. 1 locks the blocking device against opening. For purposes of illustration, bar 6 is shown in the turning plane of the excenter 3, but it may be practical to arrange it perpendicular thereto, to enter a hole in the excenter 3 and another hole in a fixed console aligned thereto (not shown). The bar 6 is resiliently powered by a compression spring 14 against fixed console 13 and spring seat 12 on bar 6.

Bar 6 is moved to its locking position by means of displacement device D through lever 10 and a shoulder 7 on bar 6, against the force of spring 14. The displacement-device, schematically shown in FIG. 1, comprises a diaphragm which is on one side pressurized from vessel 1 via a tube 9, and the diaphragm when pressurized moves a lever 15 which works on shoulder 7.

In order to make this locking device fail-safe there is a second locking device with a shoulder 10 on bar 6, cooperating with a locking bolt 11 which is manoeuvered electromechanically with a magnetic lock device.

Figure 2:
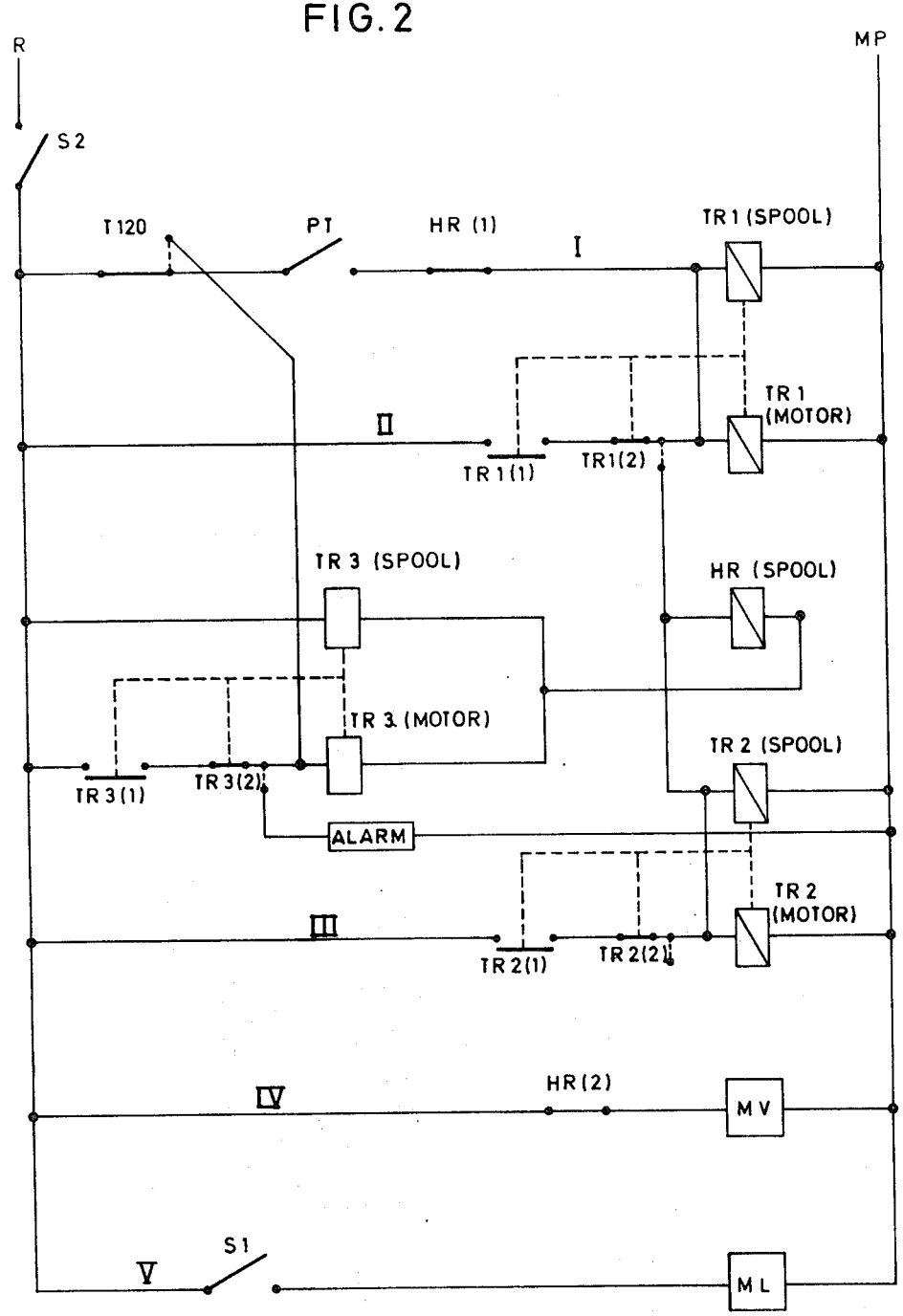
FIG. 2 shows a schematic wiring diagram.

The functioning of the various devices is shown in FIG. 2. This is a circuit with interlocking functions which will now be described. There are, besides the devices described with reference to FIG. 1, further three time relays TR1, TR2, TR3 and an ordinary relay HR.

The time relays are each provided with an activation winding and a motor. When the activation winding receives a current, a first contact is closed for providing the motor with current, and after a predetermined time, a second contact is switched, disconnecting the motor, and the first contact is opened, whereafter the time relay is ready for a new period.

Controlling the circuit is the microswitch S2, so that the circuit will not be energized until the lid of the vessel is closed (cf. FIG. 1). We may now study the function of the circuit where branches marked I–V are discernible.

In branch I, thermostat switch T120 and pressure sensor PT are coupled in series with a normally closed contact HR(1) belonging to relay HR. Sensor PT closes when the vessel is under substantial pressure, and thermostat T120 will switch from its shown position at a predetermined temperature.

Suppose now that the vessel 1 in FIG. 1 is provided with steam via tube 4 after the lid has been closed and blocked, thereby closing microswitch S2. There will then be current in branch IV of FIG. 2, and the magnetic valve MV will close. Pressure in vessel 1 augments, and pressure sensor switch PT will close. As T120 is in its position in FIG. 2, being cold, there will be current in branch I, and time relay TR1 is activated. This relay normally has a preset time of 5–6 seconds (if thermostat T120 is of chrome-nickel steel), during which time its motor will receive current. After that time it will switch contact TR1(2) to its dashed position (FIG. 2), activating relay HR, which will open its contacts HR(1) and HR(2). This breaks the current in branch I and also in branch IV, the latter leading to the opening of magnet valve MV which will release air, condensed water and possibly steam. Simultaneously, time relay TR2 is activated, closing contact TR2(1) so that relay HR will receive independently a current from branch III during the predetermined time of time relay TR2. Thus, relay HR will stay down and the magnet valve MV will stay open at least as long as that predetermined time. After that time the magnet valve will close because time relay TR2 goes to its indicated start position, and in case thermostat T120 is now hot, its contact will have switched to its closed position, causing branch I to be disconnected. In the opposite case, branch I will activate time relay TR1 anew, and if, after its preset time has lapsed, thermostat T120 is still not hot, the same sequence will be completed anew.

It should be explained that the main idea with the function so far described is to guarantee a proper filling of vessel 1 with steam, without air and condensed water. In function, thermostat T120 will periodically cool down and activate a new cycle which ends when it becomes hot anew. The predetermined time of time relay TR2 is determined by the length and configuration of the evacuation tube 5 but should be at a minimum of 5 seconds.

Time relay TR3 is a timer unit and is activated by thermostat T120 switching to its dashed position, and it will measure the total time when the thermostat has been hot. When a preset time of this time relay has lapsed, the motor of which stops when the temperature is low, an alarm signal is activated indicating the end of a treatment cycle (for instance a sterilization cycle or a vulcanization or heat curing cycle).

As is apparent from FIG. 2, sensor S1 will close the magnet lock ML as soon as a predetermined condition is sensed. In the embodiment described, this sensor is a temperature sensor set slightly over 100° C. This means that the second locking device ML, 10, 11 of FIG. 1 will activate.

This construction has several security functions. It is particularly noted that the magnetic valve MV is such that it opens whenever there is a mains failure, and will thus be a security valve.

Further, it is noted that, as long as displacement device D receives pressure from the vessel, the blocking mechanism of the lid will be locked. Even if there is a failure of displacement device D (e.g., due to a ruptured membrane), there is still a second locking device ML, 10, 11 which will lock the first locking device. Thus, there would have to be a malfunction in both systems in order for the system to fail. Even if the displacement device D fails simultaneously with a mains failure, there is considerable safety left since the magnetic valve MV will open for good thereby depressurizing the vessel 1.

It is clear that this concept of a fail-safe construction comprising a blocking mechanism, a first locking device for the blocking device and working on pressure and a second locking device which locks the first locking device may be useful for all kinds of lids and covers for pressure vessels which are opened manually and where there is a risk of inadvertent opening.

Figure 3:
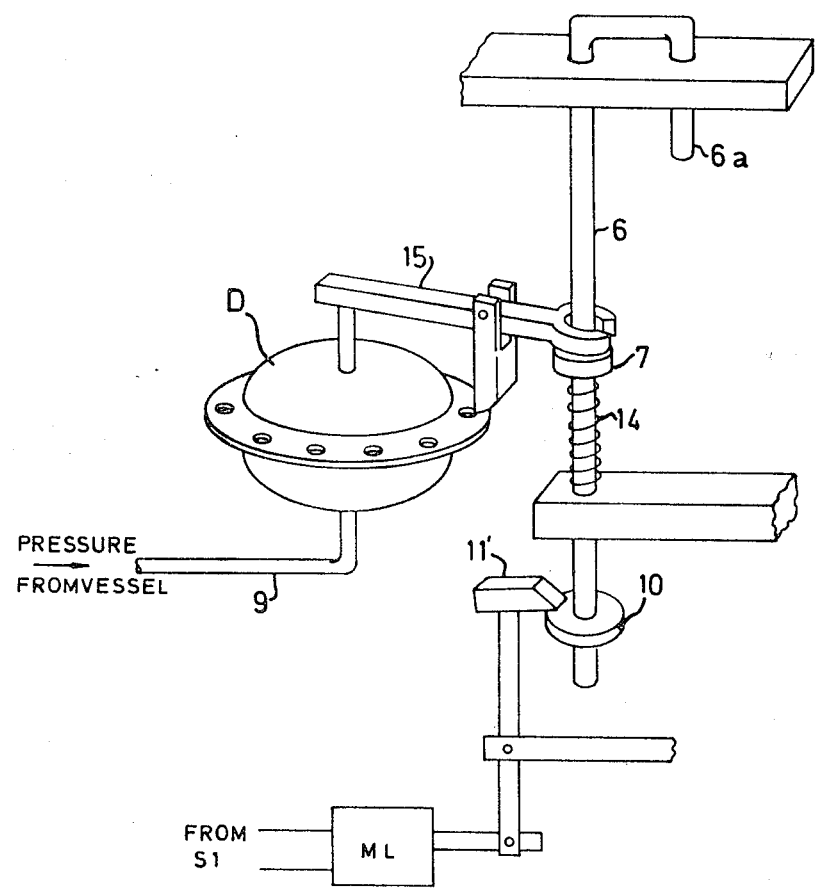
FIG. 3 shows a detailed embodiment of a fail-safe locking device.

FIG. 3 schematically shows a double locking device where a locking bar 6 is bent and arranged in a fixed console such that its end 6a as shown may be inserted in a hole in e.g., an excenter (as shown at 3 in FIG. 1). In FIG. 3, the device is double locking as pressure-sensing displacement device D forces the bar 6 downward via lever 15, and the bar 6 is further locked by lock piece 11' which is governed by the magnetic lock ML via a lever.

As shown, the displacement device is a membrane unit well-known in the art, which may be provided with a plane rubber membrane or bellows, activated from one side by the vessel pressure via a tube 9. Such a displacement device may be custom ordered or even brought from the shelf from several manufacturers. Although at present such a membrane unit is preferred, it is also possible to use a system with a plunger or the like, although a membrane system has the inherent advantage of tightness as long as it is functioning properly. It is preferred to let this displacement device activate at a pressure of 0.2–0.3 bars, which is easily obtained by giving the membrane an appropriate diameter in consideration of the size of locking bar 6.

What I claim is:

1. In a fail-safe device for a lid of a pressure vessel having an evacuation conduit, said lid having a blocking mechanism for blocking said lid against opening as a result of internal pressure in said vessel, said blocking mechanism being switchable from a blocking state to an unblocking state for enabling said lid to be opened, the improvement comprising (a) a first sensor means for sensing that said blocking mechanism is in its blocking state, said first sensor means controlling an electrically operated valve in said evacuation conduit whereby to enable immediate depressurization of said pressure vessel upon indication by said first sensing means that said blocking mechanism is not in said blocking state;

(b) a first locking device switchable between a locking position for locking said blocking mechanism in said blocking state and an unlocking position in which said blocking mechanism is unlocked;

(c) a displacement device in communication with the interior of said vessel and coupled to displace said first locking device against resilient means into said locking position when a predetermined pressure prevails inside said vessel;

(d) a second sensor means for sensing a predetermined condition inside said vessel and for emitting an electrical signal at said condition;

(e) an electromechanical transducer coupled to receive said electrical signal for generating a force; and (f) a second locking device coupled to said electromechanical transducer for moving into a locking position for locking said first locking device in its said locking position when receiving said force.

2. The combination according to claim 1, wherein said second sensor means for sensing a predetermined condition is a temperature sensor for sensing hot pressurized vapor inside said vessel.

3. The combination according to claim 1, wherein said second sensor means for sensing a predetermined condition is a pressure sensor for sensing pressure inside said vessel.

4. In a fail-safe device for a lid of a pressure vessel having an evacuation conduit, said lid having a blocking mechanism for blocking said lid against opening as a result of internal pressure in said vessel, said blocking mechanism being switchable from a blocking state to an unblocking state for enabling said lid to be opened, the improvement comprising (a) a first sensor means for sensing that said blocking mechanism is in its blocking position, said first sensor means controlling an electrically operated valve in said evacuation conduit whereby to enable immediate depressurization of said pressure vessel upon indication by said first sensing means that said blocking mechanism is not in said blocking state;

(b) a first locking device switchable between a locking position for locking said blocking mechanism in said blocking state and an unlocking position in which said blocking mechanism is unlocked;

(c) a displacement device in communication with the inside of said vessel and coupled to displace said first locking device against resilient means into said locking position when a predetermined pressure prevails in said vessel;

(d) a second sensor means for sensing a predetermined condition inside said vessel and for emitting an electrical signal at said condition;

(e) electromechanical transducer coupled to receive said electrical signal for generating a force, said force being coupled to move a second locking device into a locking position for locking said first locking device in its said locking position;

(f) an electrically operated valve coupled in a venting tube in said vessel, said valve being open when unactivated;

(g) a pressure sensor and a temperature sensor for sensing pressure and temperature in said venting tube upstream of said venting tube valve and for emitting signals when a limit temperature and a limit pressure, respectively, are obtained; and (h) means for sensing said signals and for closing said venting tube valve when both said signals are present.

5. The combination according to claim 4, wherein said means for sensing said signals comprise a first time relay for emitting a delayed signal when one of said signals is lacking, a second time relay for sensing said delayed signal for opening said venting tube valve for a predetermined time and for simultaneously passivating said first time relay.

* * * * *